(12) United States Patent
Wang et al.

(10) Patent No.: US 8,991,272 B2
(45) Date of Patent: Mar. 31, 2015

(54) DETECTING DEVICE FOR RECOVERY OF RELEASE FILM AND RECOVERY APPARATUS FOR RELEASE FILM

(75) Inventors: Jinjun Wang, Beijing (CN); Kweonho Park, Beijing (CN); You Zheng, Beijing (CN); Haibin Liu, Beijing (CN); Xu Li, Beijing (CN); Yujie Wang, Beijing (CN)

(73) Assignees: Boe Technology Group Co., Ltd., Beijing (CN); Hefei Boe Optoelectronics Technology Co., Ltd., Hefei, Anhui (CN)

( * ) Notice: Subject to any disclaimer, the term of this patent is extended or adjusted under 35 U.S.C. 154(b) by 311 days.

(21) Appl. No.: 13/482,216

(22) Filed: May 29, 2012

(65) Prior Publication Data
US 2012/0304785 A1  Dec. 6, 2012

(30) Foreign Application Priority Data

Jun. 2, 2011 (CN) .................. 2011 2 0184940 U

(51) Int. Cl.
*G01N 1/00* (2006.01)
*G01D 5/34* (2006.01)
*G01N 33/00* (2006.01)

(52) U.S. Cl.
CPC ............... *G01D 5/342* (2013.01); *G01N 33/00* (2013.01)
USPC .......................................................... 73/865.8

(58) Field of Classification Search
CPC ...... G01N 33/00; G01N 21/954; G01D 21/00
USPC .......................................................... 73/865.8
See application file for complete search history.

(56) References Cited

U.S. PATENT DOCUMENTS

| 2,521,427 | A | * | 9/1950 | Victor ........................ 242/356.5 |
| 2,915,256 | A | * | 12/1959 | Bruhn ........................ 242/586.4 |
| 5,891,483 | A | * | 4/1999 | Miyajima ....................... 425/89 |
| 2005/0062194 | A1 | * | 3/2005 | Kanemura ..................... 264/216 |
| 2006/0064857 | A1 | * | 3/2006 | Kumazawa et al. ............. 26/93 |
| 2007/0163699 | A1 | * | 7/2007 | Wellenhofer et al. ......... 156/184 |
| 2007/0261218 | A1 | * | 11/2007 | Kumazawa et al. ............. 26/94 |
| 2013/0133839 | A1 | * | 5/2013 | Seo et al. ..................... 156/715 |

FOREIGN PATENT DOCUMENTS

KR   1020100091524   * 10/2011   ............... G02B 5/30

* cited by examiner

*Primary Examiner* — Hezron E Williams
*Assistant Examiner* — Rodney T Frank
(74) *Attorney, Agent, or Firm* — Ladas & Parry LLP

(57) ABSTRACT

Embodiments of the disclosed technology provide a detecting device for recovering of release film and a recovery apparatus for release film. The recovery apparatus comprises clips for gripping release film, the detecting device comprises: a detecting sensor; a mobile module coupled onto one clipping arm of the clip. When the release film is gripped by the clip, the release film shifts the mobile module to a first position where the mobile module portion enters the detection scope of the detecting sensor; when the release film is not gripped by the clip, the mobile module shifts to a second position, where the whole mobile module portion withdraws out of the detection scope of the detecting sensor.

12 Claims, 3 Drawing Sheets

DETECTING DEVICE FOR RECOVERY OF RELEASE FILM AND RECOVERY APPARATUS FOR RELEASE FILM

BACKGROUND

One or more embodiment of the disclosed technology relate to a detecting device for the recovery of release film and a recovery apparatus for release film.

When a polarizer release film is recovered in a conventional technology, the release film is detected in the following way. When clips grip the release film such that the top end of a photoelectric transducer is covered, and when the detected value is greater than a preset value, the result that the clips have gripped the release film can be obtained, and the recovery can be achieved.

However, there are some disadvantages in this conventional technology. Because the position of release film is uncertain in recovery, the sensing area of photoelectric transducer on the release film is larger when performing detection on the release film, which increases error-sensing rate of the transducer. If the detection of release film failed, it is necessary that the operators enter the recovery apparatus to conduct maintenance frequently, which in turn gives rise to the related defectiveness after a polarizer sheet has been attached; and if the fail times of the detection of release film increased, there will be a great adverse influence on the activation or utilization of the recovery apparatus.

SUMMARY

In connection with the conventional technology, it is necessary to provide a detecting device for the recovery of release film and a recovery apparatus for release film for increasing the detecting success rate during the recovery of a polarizer release film for example.

An aspect of the disclosed technology provides a detecting device for recovering of release film, capable of being adapted in a recovery apparatus for release film, which recovery apparatus comprises clips for gripping release film, the detecting device comprises: a detecting sensor; a mobile module coupled onto one clipping arm of the clip. When the release film is gripped by the clip, the release film shifts the mobile module to a first position where the mobile module portion enters the detection scope of the detecting sensor; when the release film is not gripped by the clip, the mobile module shifts to a second position, where the whole mobile module portion withdraws out of the detection scope of the detecting sensor.

According to another aspect of the disclosed technology further provides a recovery apparatus for release film, comprising a clip for gripping release film and a detecting device for the recovery of release film, and the detecting device comprises: a detecting sensor; a mobile module coupled onto one clipping arm of the clip. When the release film is gripped by the clip, the release film shifts the mobile module to a first position where the mobile module portion enters the detection scope of the detecting sensor; when the release film is not gripped by the clip, the mobile module shifts to a second position, where the mobile module portion withdraws out of the detection scope of the detecting sensor.

In one or more embodiments, when the release film is gripped by the clip, the release film shifts the mobile module to a first position, where the mobile module portion enters the detection scope of the detecting sensor; when the release film is not gripped by the clip, the whole mobile module shifts to a second position, where the whole mobile module portion withdraws out of the detection scope of the detecting sensor. In the embodiments of the disclosed technology, in despite of the location(s) of release film, the mobile module can surely enter the detection scope of the detecting sensor only if the clip grips a release film, such that original detecting mode for release film without a fixed scope in the conventional technology is converted into a detecting mode for the mobile module, thus unnecessary detecting area can be decreased, the detecting success rate of sensor can be greatly improved, and therefore the activation of recovery apparatus can be increased.

Further scope of applicability of the disclosed technology will become apparent from the detailed description given hereinafter. However, it should be understood that the detailed description and specific examples, while indicating preferred embodiments of the disclosed technology, are given by way of illustration only, since various changes and modifications within the spirit and scope of the disclosed technology will become apparent to those skilled in the art from the following detailed description.

BRIEF DESCRIPTION OF THE DRAWINGS

The disclosed technology will become more fully understood from the detailed description given hereinafter and the accompanying drawings which are given by way of illustration only, and thus are not limitative of the disclosed technology and wherein.

DETAILED DESCRIPTION

In order to make clearer the technical problems, technical solutions to be solved by the embodiments of the disclosed technology, and advantages of the embodiments, a detailed description will be made with reference to the accompanying drawings.

The embodiments of the disclosed technology are conducted in connection with the problem in the conventional technology that the sensing area of photoelectric transducer on the release film is larger when performing detection of release film, thus increase error-sensing rate of the transducer. The embodiments provide a detecting device for the recovery of release film and a recovery apparatus for release film, which are able to increase the detecting success rate on release film during the recovery of a polarizer release film for example.

One embodiment of the disclosed technology provides a detecting device for recovering of release film, adapted in a recovery apparatus for release film, which apparatus comprises a clip for gripping a release film, the detecting device comprises: a detecting sensor; a mobile module coupled onto one clipping arm of the clip. When the release film is gripped by the clip, the release film shifts the mobile module to a first position, where the mobile module portion enters the detection scope of the detecting sensor; when the release film is not gripped by the clip, the mobile module shifts to a second position, where the whole mobile module portion withdraws out of the detection scope of the detecting sensor.

In the detecting device for the recovery of release film according to the embodiment of the disclosed technology, when the release film is gripped by the clip, the release film shifts the mobile module to a first position, the mobile module portion enters the detection scope of the detecting sensor; when the release film is not gripped by the clip, the mobile module shifts to a second position, where the whole mobile module portion withdraws out of the detection scope of the detecting sensor. In the embodiment of the disclosed technology, in despite of the location(s) of a release film, the mobile module can surely enter the detection scope of the detecting sensor only if the clip grips the release film, such that the original detecting mode for a release film without a fixed scope in the conventional technology is converted into a detecting mode for the mobile module, thus the unnecessary detecting area is decreased, the detecting success rate of sensor greatly can be improved, and therefore the activation of recovery apparatus increased. The example of the detecting sensor comprising position transducer, photoelectrical transducer, and the like.

Figure 1:
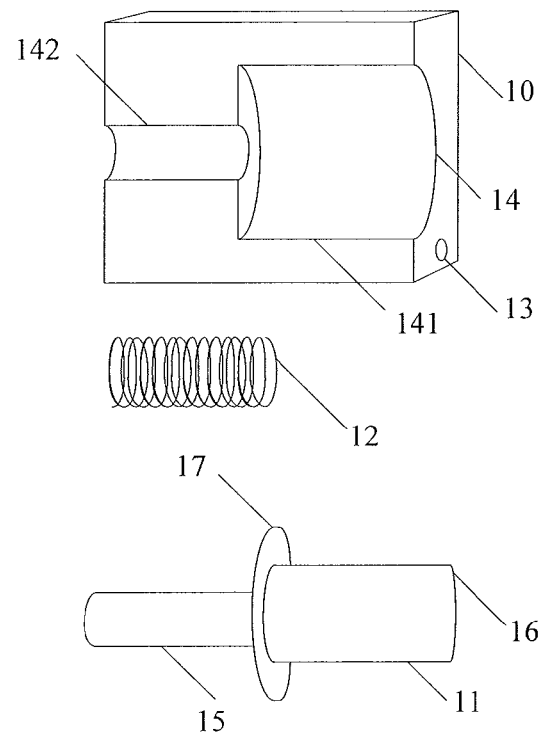
FIG. 1 is an exploded schematic view of a mobile module according to an embodiment of the disclosed technology.

Further, FIG. 1 shows an exploded schematic view of an exemplary mobile module, and the mobile module comprises: a fixture block 10 fixed onto a clipping arm; a bearing 11 provided into the fixture block and able to reciprocate along the cylinder within the fixture block; and a spring 12 arranged around the bearing 11 with one end thereof contacting the bottom of the cylinder and the other end contacting with the intermediate step of the bearing.

Further, the fixture block 10 also comprises a screw hole 13 thereon so that the fixture block 10 can be held onto the clipping arm by screws. The fixture block has a cylinder 14 comprising two parts, of the first part 141 has a diameter less than that of the second part 142. The bearing 11 comprises a top end 15 and a distal end 16, and as shown in FIG. 1, the diameter of the top end 15 is less than that of the distal end 16, and a step 17 is provided between the top end 15 and the distal end 16 in the midway of the bearing 11. The diameter of spring 12 is greater than the diameter of the second part 142 of the cylinder but less than that of the step 17.

The bearing 11 is an example of a movable part in the embodiment, the spring 12 is an example of a position returning part for realizing the reciprocating of the movable part, and the step 17 on the bearing is an example of the supporting member on the movable part. However, it should be understood the disclosure is not limited to these specific examples as shown in the drawings.

Figure 2:
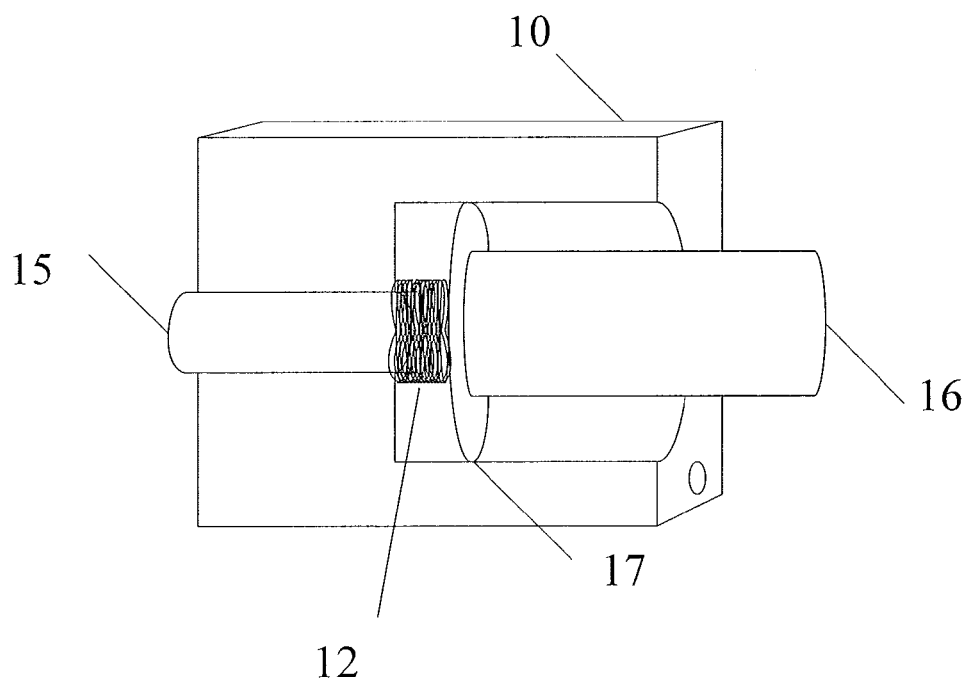
FIG. 2 is a schematic combination view of the mobile module according to the embodiment of the disclosed technology.

FIG. 2 illustrates an assemble schematic view of the mobile module, the top end 15 of the bearing can perform a reciprocating movement within the cylinder 14 of the fixture block 10, the spring 12 is sheathed onto the top end 15 of the bearing 11 with one end against the second part 142 of cylinder and the other end against the intermediate step 17 of the bearing 11.

Figure 3:
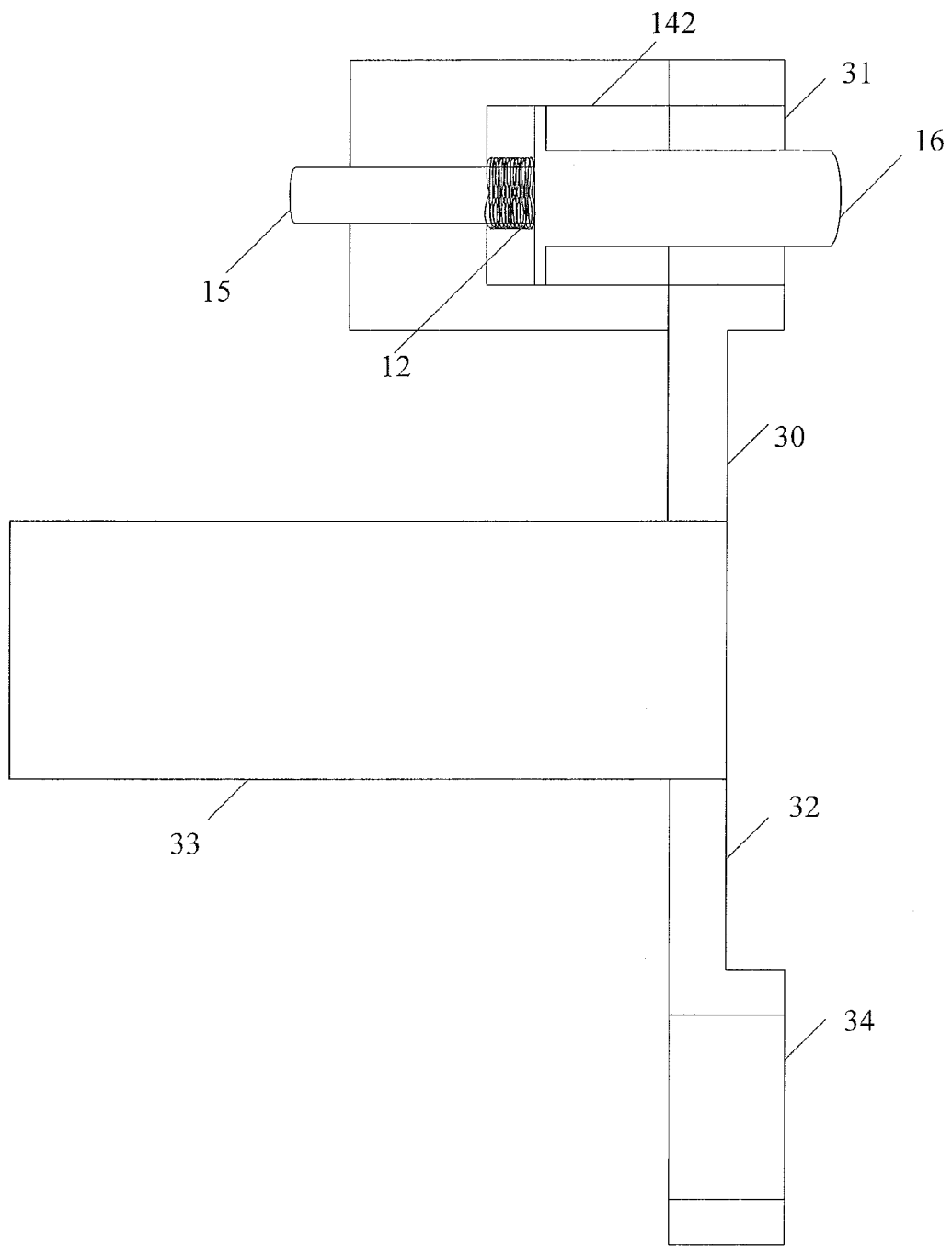
FIG. 3 is schematic section view of the mobile module according to embodiment of the disclosed technology while fixed onto clipping arms of the clip.

FIG. 3 illustrates a sectional schematic view of the mobile module fixed onto the clipping arm of a clip. In the detecting device for the recovery of release film of the embodiment of the disclosed technology, two clipping arms 30 and 32 connected with each other through a revolution (or rotation) module 33, which can control the two clipping arms to rotate by 90° such that the two clipping arms can grip a release film therebetween. There is a through hole 31 on clipping arm 30 and a through hole 34 on clipping arm 32, when the fixture block 10 is fixed onto a clipping arm, the second part 142 of the cylinder corresponds to the through hole 31, and when clips do not grip any release film, the distal end 16 of the bearing 11 locates into the through hole 31.

Figure 4:
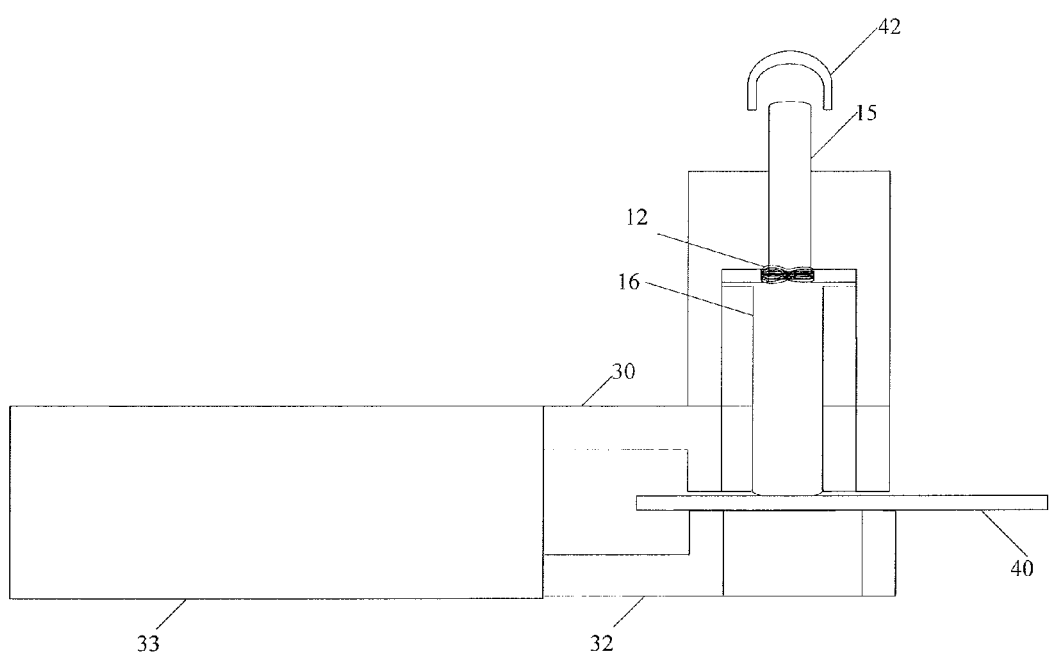
FIG. 4 is a schematic view of a clip in closing state according to embodiment of the disclosed technology.

FIG. 4 illustrates a schematic view when the clip remains in a closing state, in which a detecting sensor 42 is disposed over the bearing 11, and compared with FIG. 3, the revolution module 33 control the clipping arms to rotate by 90°, such that the clipping arms grip the release film 40. During the gripping, the release film 40 moves the bearing 11 in the direction away from the through hole 31, the spring 12 compressed, the distal end 16 of the bearing 11 withdraws out of the through hole 31, and the top end 15 of the bearing 11 enters into the detection scope of the detecting sensor 42, thus it can be determined that the clip has gripped the release film 40 and the recovery of release film can be successfully conducted.

If the revolution module 33 closes the two clipping arms together but fails to grip a release film, a part of the distal end 16 of the bearing 11 enters into the corresponding through hole 34 of the clipping arm 32, while the top end 15 of the bearing 11 leave away from, i.e., is absent from, the detection scope of the detecting sensor 42, thus it can be determined that the clips do not grip any release film and the recovery of release film fails.

When the release film is brought to a recovery spot, the revolution module 33 controls the two clipping arms open, and the bearing 11 moves in the direction of the through hole 31 while driven by the spring 12, such that the distal end 16 of the bearing 11 enters the through hole 31 and the top end 15 of the bearing 11 withdraws out of the detection scope of the detecting sensor 42.

Another embodiment of the disclosed technology further provides a recovery apparatus for a release film, which comprises the above-described detecting device for the recovery of release film.

Since a large sensing scope for release film is required in the conventional technology, a sensor of photo-electricity reflection type is always needed to detect a release film, inducing a higher cost; in contrast, the detecting sensor of the embodiment of the disclosed technology only needs detecting the cross section of the top end of a bearing, thus the sensing scope is reduced greatly, a simple sensor therefore can be adopted, for example, position transducer, causing a reduction of cost.

In the exemplary detecting device for recovery of release film and the recovery apparatus for release film according to the embodiments of the disclosed technology, when the release film is gripped by the clip, the release film moves the bearing in the direction away from the through hole of the clipping arm, and the top end of the bearing enters the detection scope of the detecting sensor; when the release film is not gripped by the clips, the spring drives the bearing in the direction of the through hole, such that the distal end of the bearing enters into the through hole of the opposite clipping arm while the top end of the bearing withdraws out of the detection scope of the detecting sensor. In the case of the embodiment of the disclosed technology, in despite of the positions of the release film, the top end of the bearing can surely enter the detection scope of the detecting sensor only if the clip grips the release film, such that the original detecting mode for release film without a fixed scope is converted into a detecting mode for the cross-section of the top end of the bearing, thus unnecessary detecting area can be decreased, the detecting success rate of the sensor can be improved greatly, and equipment failure rates caused by the detection failure for release film can be depressed enormously, thereby equipment activation can be extremely increased, the times for the operators enters equipment for maintenance can be reduced, causing reduction of defectiveness.

The described above are part of the embodiments of the disclosed technology, it should be noted the ordinary skilled in conventional technology could make any improvements and modifications, which also should be regarded as the protective scope of the disclosed technology, without departing from the principle of the embodiments of the disclosed technology.

What is claimed is:

1. A detecting device, capable of being adapted in a recovery apparatus for a release film, the recovery apparatus comprising a clip for gripping the release film, the clip having a first clipping arm and a second clipping arm, the detecting device configured for detecting recovery of the release film and comprising:
   a detecting sensor; and
   a mobile module coupled onto the first clipping arm of the clip;
   wherein when the release film is gripped by the clip, the release film shifts the mobile module to a first position where the mobile module partly enters a detection scope of the detecting sensor; and
   when the release film is not gripped by the clip, the mobile module shifts to a second position where the mobile module wholly withdraws out of the detection scope of the detecting sensor.

2. The detecting device according to claim 1, wherein the mobile module comprises:
   a fixture block fixed onto the first clipping arm and having a cylinder corresponding to a through hole of the first clipping arm;
   a movable part provided into the fixture block and being able to reciprocate along the cylinder within the fixture block; and
   a position returning part;
   wherein when the release film is gripped by the clip, the release film moves the movable part in the direction away from the through hole such that a top end of the movable part enters the detection scope of the detecting sensor; and
   when the release film is not gripped by the clip, the position returning part drives the movable part move in the direction towards the through hole such that the top end of the movable part withdraws out of the detection scope of the detecting sensor.

3. The detecting device according to claim 1, further comprising:
   a revolution module connected to the first and second clipping arms of the clip and configured for controlling the first and second clipping arms to grip the release film.

4. The detecting device according to claim 2, wherein the movable part has a distal end opposite to the top end, and the diameter of the top end of the movable part is less than that of the distal end of the movable part.

5. The detecting device according to claim 2, wherein the position returning part is a spring arranged around the movable part with one end thereof contacting a bottom of the cylinder and another end thereof contacting a supporting member of the movable part.

6. The detecting device according to claim 5, wherein the supporting member of the movable part is a step provided between the top end and the distal end of the movable part.

7. A recovery apparatus for a release film, comprising:
   a clip for gripping the release film, the clip having a first clipping arm and a second clipping arm, and
   a detecting device configured for detecting recovery of the release film, which comprises:
   a detecting sensor; and
   a mobile module coupled onto the first clipping arm of the clip;
   wherein when the release film is gripped by the clip, the release film shifts the mobile module to a first position, where the mobile module partly enters a detection scope of the detecting sensor; and
   when the release film is not gripped by the clip, the mobile module shifts to a second position, where the mobile module wholly withdraws out of the detection scope of the detecting sensor.

8. The recovery apparatus according to claim 7, wherein the mobile module comprises:
   a fixture block fixed onto the first clipping arm and having a cylinder corresponding to a through hole of the first clipping arm;
   a movable part provided into the fixture block and able to reciprocate along the cylinder within the fixture block; and
   a position returning part;
   wherein when the release film is gripped by the clips, the release film moves the movable part in the direction away from the through hole such that a top end of the movable part enters the detection scope of the detecting sensor; and
   when the release film is not gripped by the clips, the position returning part drives the movable part move in the direction towards the through hole such that the top end of the movable part withdraws out of the detection scope of the detecting sensor.

9. The recovery apparatus according to claim 7, wherein the detecting device for the recovery of release film further comprises:
   a revolution module connected to the first and second clipping arms of the clip and configured for controlling the first and second clipping arms to grip the release film.

10. The recovery apparatus according to claim 7, wherein the movable part has a distal end opposite to the top end, and the diameter of the top end of the movable part is less than that of the distal end of the movable part.

11. The recovery apparatus according to claim 7, wherein the position returning part is a spring arranged around the movable part with one end thereof contacting the bottom of the cylinder and another end thereof contacting a supporting member of the movable part.

12. The recovery apparatus according to claim 11, wherein the supporting member of the movable part is a step provided between the top end and the distal end of the movable part.

* * * * *